United States Patent [19]

Zelger et al.

[11] Patent Number: 6,133,215
[45] Date of Patent: *Oct. 17, 2000

[54] FLUORESCENT WHITENING AGENT

[75] Inventors: Josef Zelger, Riehen; Andreas Burkhard, Basel, both of Switzerland; Serge Schroeder, Rosenau; Bernard Schultz, St Louis, both of France

[73] Assignee: Ciba Specialty Chemicals Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/140,234

[22] Filed: Aug. 26, 1998

[30] Foreign Application Priority Data

Aug. 28, 1997 [GB] United Kingdom ............... 9718081

[51] Int. Cl.$^7$ ................................ C11D 9/44; C11D 3/42
[52] U.S. Cl. ....................... 510/326; 510/324; 510/325; 510/394; 252/301.21; 562/45; 562/88
[58] Field of Search ................... 252/301.21; 562/45, 562/88; 510/324, 325, 326, 394

[56] References Cited

U.S. PATENT DOCUMENTS 4,130,498  12/1978  Lee et al. .......................... 252/99

FOREIGN PATENT DOCUMENTS 2076011  11/1981  United Kingdom .
92/06172   4/1992  WIPO .

OTHER PUBLICATIONS

Derwent Abstract No. 76–96964X [52] of JP 51129403 Nov. 11, 1976.
Derwent Abstract No. 76–15867X [09] of JP 51005308 Jan. 17, 1976.

Chem. Abstr. 86:57144e (1977) Mar. 7, 1977 Okumura et al "Granular detergent compositions" p. 113 No. 10.

Chem. Abstr. 84:152613z (1976) May 31, 1976 Yagi et al "White Synthetic detergent" No. 22 p. 122.

*Primary Examiner*—Mark Kopec
*Assistant Examiner*—Brian P. Mruk
*Attorney, Agent, or Firm*—Kevin T. Mansfield

[57] ABSTRACT

There is provided a white crystal form of the compound having the formula:

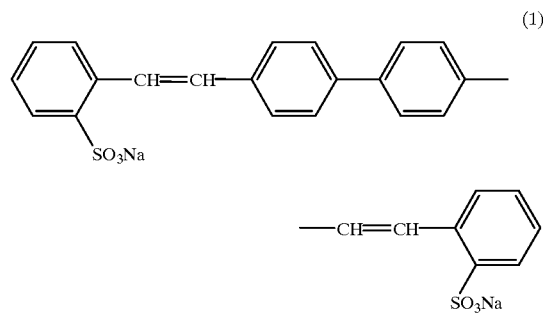

whose crystal form is characterised by an X-ray diffraction diagram which is essentially as shown in Table I, II or III. Also provided is a formulation comprising from 10 to 85% by weight of the white crystal form of compound having the formula (1) and from 90 to 15% by weight of a polyhydroxy compound, preferably glycerine.

35 Claims, No Drawings

FLUORESCENT WHITENING AGENT

The present invention relates to a new fluorescent whitening agent, in particular to a new white crystal form of a disodium salt of a distyrylbiphenyl disulfonic acid, processes for its production and its use in the fluorescent whitening of substrates such as paper, textile materials and, especially, detergents.

The fluorescent whitening agent having the formula:

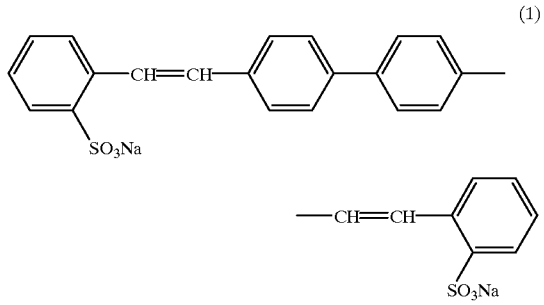

(1)

has excellent fluorescent whitening properties and is widely used, for example, as a fluorescent whitening ingredient in detergent compositions.

As normally manufactured, however, the compound of formula (1) has a yellowish tinge which, depending on the method of detergent manufacture, can impart a slight discolouration to the finished detergent.

Various attempts have been made to reduce the yellow tinge of the compound of formula (1). For example, in GB-A-2,076,011 it is stated that diphenyl and stilbene brighteners which have a yellowish hue combine with a hydroxyl-containing compound and are rendered substantially white. In Example 1, of GB-A-2,076,011 there is described a screening test to determine which hydroxyl-containing compound was effective in rendering white a yellow diphenyl or stilbene brightener. Among the hydroxyl-containing compounds which were tested and found to be effective are ethanol and glycerine. The use of ethanol and other hydroxyl-containing compounds has the disadvantage, however, that when the solvent is removed from the said solution formulation, prior to the incorporation of the compound of formula (1) into the final substrate, the residual compound of formula (1) reverts back to its original yellow-tinged form.

Surprisingly, it has now been found that the formulation of the compound of formula (1) together with a polyhydroxy compound, in particular glycerine, provides a solution which contains a new white crystal form of the compound of formula (1). As a consequence, a detergent which contains the new white crystal form of the compound of formula (1) exhibits a very desirable, improved white aspect.

Accordingly, the present invention provides as a first aspect, a white crystal form of the compound having the formula (1), whose crystal form is characterised by an X-ray diffraction diagram which is essentially as shown in Table I or Table II or a mixture of white crystals whose crystal forms are characterised by an X-ray diffraction diagram which is essentially as shown in Table III.

The X-ray diffraction patterns of Tables I, II and III were produced with a powder diffractometer using Cu—K60 1 radiation.

The white crystal form of the compound having the formula (1) may be produced by contacting the compound having the formula (1) with a polyhydroxy compound in a weight ratio of 10 to 85% of the compound having the formula (1) to 90 to 15% of polyhydroxy compound. Depending on the reaction conditions, crystals of modification N (Table I), crystals of modification O(Table II) or a mixture of crystals of modification O and V (Table III) are obtained.

Crystals of modification N are for example produced by first contacting the compound having the formula (1) with ethanol and subsequently adding the polyhydroxy compound. After removal of the ethanol, examination of the resulting composition indicates that it contains the new white crystal form of the compound having the formula (1) corresponding to modification N which is characterised by an X-ray diffraction diagram which is essentially as shown in Table I.

Crystals of modification O are for example produced by first contacting the compound having the formula (1) with water and subsequently adding the polyhydroxy compound in an amount of at least 1 parts of polyhydroxy compound per 1 part of compound of the formula (1). After being allowed to stand for at least 1 hour at a temperature of above 40° C., preferably above 45° C., the resulting mixture is allowed to cool to 20° C. The residue contains the new white crystal form of the compound having the formula (1) corresponding to modification O which is characterised by an X-ray diffraction diagram which is essentially as shown in Table II.

The mixture of crystals of modifications O and V (Table II) can be obtained by a process similar to the process for the preparation of modification O, but not exceeding a temperature of 25° C. and/or adding at most 1 part of polyhydroxy compound per 1 part of compound of the formula (1).

The polyhydroxy compound may be, e.g., a glycol such as ethylene glycol, diethylene glycol or propylene glycol, or a triol such as 1,2,6-hexanetriol or, especially glycerine or an oligomer of glycerine, e.g. a di-, tri- or polyglycerine. The present invention provides, as a second aspect, a new formulation comprising from 10 to 85% by weight of the white crystal form of the compound having the formula (1) and from 90 to 15% by weight of a polyhydroxy compound. Preferably, the new formulation comprises from 30 to 60%, more preferably from 40 to 60% by weight of the white crystal form of the compound having the formula (1) and from 70 to 40%, more preferably from 60 to 40% by weight of a polyhydroxy compound. It is especially preferred that the new formulation according to the present invention comprises about 50% by weight of the white crystal form of the compound having the formula (1) and about 50% by weight of a polyhydroxy compound.

Depending on the relative proportions of the white crystal form of the compound having the formula (1) and polyhydroxy compound in the liquid formulation according to the present invention, the new formulation may have an undesired tacky property. Since such a tacky property could be disadvantageous when incorporating the new formulation into a final powder-form substrate, especially a powder-form detergent composition, the new formulation preferably comprises an absorbent filler or carrier. The absorbent filler/carrier has the effect of removing any tackiness from the new formulation of the invention and converting it into a dry, pourable material.

Examples of such absorbent fillers/carriers include, e.g., an inorganic salt such as sodium chloride, sodium sulfate, sodium carbonate or trisodium citrate, a further hydroxy group-containing compound such as citric acid, neopentyl alcohol, PEG (polyethyleneglycol) 200, PEG 300, PEG 400, PEG 600, PEG 4000, PEG 550 monomethyl ether, PEG 1500 monomethyl ether, PEG 2000 monomethyl ether or PEG 5000 monomethyl ether, copolymers from ethylene oxide and propylene oxide or a solid carbohydrate such as D-sorbitol and sugar. Preferred, however, the following materials which are solid at 25° C., namely kaolin, layer-lattice silicates, a Mg/Al silicate, especially bentonite, montmorillonite, a zeolite, a highly dispersed silicic acid, cyclodextrin or a highly dispersed, solid, water- insoluble urea-formaldehyde resin comprising 1 mole of urea and 1.3 to 2 moles of formaldehyde, which is present in highly disperse form, having a mean particle diameter of 1 to 20 microns and having a specific BET surface of 5 to 100 m$^2$/g. Such urea-formaldehyde resins are described in more detail in U.S. Pat. No. 4,130,498. In addition to its function as an absorbent filler, the urea-formaldehyde resin also impart excellent flow properties to a solid compact detergent and, by virtue of its free methylol groups, provides a vehicle by which other desirable detergent active ingredients, such as colour-care additives and perfumes, could be incorporated, in a more permanent manner, into the final solid compact detergent. It is selfevident that also mixtures containing two or more of the above fillers can be used. Preferably, the new formulation comprises from 5 to 40%, more preferably from 10 to 30% by weight of the filler if the formulations are liquid. Solid formulations contain preferably about 10 to 80% of the filler.

The new formulation according to the present invention may also comprise one or more dispersants.

Suitable dispersants may be those of the anionic or non-ionic type. Typical examples of such dispersants are alkylbenzenesulfonates, alkyl or alkenyl ether sulfonate salts, saturated or unsaturated fatty acids, alkyl or alkylene ether carboxylate salts, sulfonated fatty acid salts or esters, phosphate esters, polyoxyethylene alkyl or alkenyl ethers, polyoxyethylene alkyl vinyl ethers, polyoxypropylene alkyl or alkenyl ethers, polyoxybutylene alkyl or alkenyl ethers, higher fatty acid alkanolamides or alkylene oxide adducts, sucrose/fatty acid esters, fatty acid/glycol monoesters, alkylamine oxides and condensates of aromatic sulfonic acids with formaldehyde, as well as lignin sulfonates or mixtures of the above cited dispersants. Nonionic surfactants, such as polyoxyethylene alkyl or alkenyl ethers, polyoxyethylene alkyl vinyl ethers, polyoxypropylene alkyl or alkenyl ethers, polyoxybutylene alkyl or alkenyl ethers, higher fatty acid alkanolamides or alkylene oxide adducts, especially lower ethylene oxide adducts with fatty alcohols, are preferred.

Optional auxiliaries which may be present in the formulation of the present invention include anti-foam agents, alkaline agents, fabric softeners, anti-redeposition agents, antioxidants, auxiliary builders such as polyacrylic acid and fragrances, organic solvents such as glycols, e.g., ethylene glycol, glycol-C$_1$–C$_4$alkyl ethers or -esters.

The formulation of the present invention may be produced by mixing the white crystal form of the fluorescent whitening agent of formula (1), glycerine, any absorbent filler, optional dispersant and optional auxiliaries, in the desired concentrations, and then homogenising the the mixture so obtained at room temperature or at elevated temperature, e.g. at 20–100° C. Mixing is conveniently effected in a suitable mixer device. Homogenisation may optionally be completed by a subsequent grinding operation.

The formulation of the present invention is particularly suitable for incorporation into a detergent composition, conveniently by adding the required, conventional amount, preferably from 0.01 to 10% by weight, of the formulation of the present invention, to a dry detergent composition, and then homogenising the mixture so obtained.

The following Examples further illustrate the present invention.

EXAMPLES 1 AND 2

At 25° C., there are sprinkled 2 g of a yellow granulate of the compound of formula (1) containing 90% by weight of active substance, 7% by weight of sodium chloride and 3% by weight of water, into 4 g of ethanol (denatured with toluene). The colour of the compound of formula (1) changes rapidly from yellow to white. 18 g of anhydrous glycerine are then added. After being allowed to stand for 1 hour at 25° C., the resulting mixture having a ratio of compound of formula (1) to glycerine of 1:9 by weight, is freed from ethanol using an infra-red drying apparatus. The resulting formulation is liquid and shows only a trace of yellow colour. X-ray examination confirms the presence of the white crystal form shown in Table I. Similar results are obtained when the ratio of compound of formula (1) to glycerine is adjusted to 2:8.

EXAMPLES 3 TO 7

The procedure described in Example 1 is repeated but using different ratios of the compound of formula (1), ethanol and anhydrous glycerine. The results obtained are set out in the following Table 1. X-ray examination in each case confirms the presence of the white crystal form shown in Table I.

TABLE 1

| Component/Property | Example 3 | Example 4 | Example 5 | Example 6 | Example 7 |
|---|---|---|---|---|---|
| A) Ethanol | 12 | 16 | 20 | 24 | 28 |
| B) Cpd of formula(1) | 6 | 8 | 10 | 12 | 14 |
| C) Glycerine | 14 | 12 | 10 | 8 | 6 |
| Ratio B:C | 3:7 | 4:6 | 5:5 | 6:4 | 7:3 |
| Aspect | fluid paste | paste | powder | powder | powder |
| Colour | white | white | white | white | white |

The results in Table 1 demonstrate that formulations according to the present invention containing precise ratios of the compound of formula (1) and glycerine provide desirable white formulations of the compound of formula (1). By contrast, when the ratio of component B:C is increased to 8:2 or 9:1, in each case an undesired yellow powder formulation is obtained. Likewise, when the compound of formula (1) is used alone, without any glycerine, a yellow granulate is obtained.

EXAMPLE 8

The following standard nonionics-free detergent composition is made up:

15.7% alkyl aryl sulfonate 3.7% fatty alcohol sulfonate 2.7% coconut acid monoethanolamide 39.0% sodium tripolyphosphate 4.0% sodium silicate 2.0% magnesium silicate 1.0% carboxymethyl cellulose 0.5% sodium ethylenediaminetetraacetate 6.7% water and sodium sulfate to make up 100%.

The formulation produced in Example 7 is dispersed in water and is added to the above-identified standard nonionics-free detergent composition to produce a detergent slurry. The formulation produced in Example 7 is added in an amount of 0.5% by weight [based on 90% active content of the compound of formula (1)] of the total detergent slurry. The detergent slurry is then dried in an oven and subsequently granulated.

The detergent so obtained has a white appearance. This white aspect is retained after storage of the detergent at 25° C. for 1 week with the exclusion of air. The whiteness of the stored detergent is determined, using a Specktraflash SF 500 instrument, and is found to be 132.

EXAMPLES 9 TO 13

At 25° C., there are sprinkled 10 g of a yellow granulate of the compound of formula (1) containing 90% by weight of active substance, 7% by weight of sodium chloride and 3% by weight of water, into 20 g of ethanol (denatured with toluene). The colour of the compound of formula (1) changes rapidly from yellow to white.

10 g of a filler are then added, followed by 10 g of anhydrous glycerine. After being allowed to stand for 1 hour at 25° C., the resulting mixture is freed from ethanol using an infra-red drying apparatus. The physical form and colour of the resulting product are then observed visually. The results obtained, using a variety of fillers, are set out in Table 2.

TABLE 2

| Filler/Aspect | Example 9 | Example 10 | Example 11 | Example 12 | Example 13 |
|---|---|---|---|---|---|
| Filler | cyclodextrin | Zeolite I | Zeolite II | Bentonite | Urea/HCHO |
| Product form | coarse powder | fine powder | fine powder | fine powder | fine powder |
| Colour | white | white | white | white | white |

Zeolite I is $Na_{12}(AlO_2)_{12}(SiO_2)_{12}.27H_2O$; Zeolite II is $Na_{86}(AlO_2)_{86}(SiO_2)_{106}..264 H_2O$; Bentonite is a Ca/Na bentonite; and Urea/HCHO is a urea/formaldehyde condensation product having a mean particle diameter of 5.7 to 6.7 microns (form agglomerates $d_{50}$) and having a specific BET surface of $17\pm3$ $m^2/g$.

X-ray examination in each case confirmed the presence of the white crystal form shown in Table I.

Similar results are obtained when the fillers used in Examples 9 to 13 are replaced by one or more of the following fillers/carriers: sodium chloride, sodium sulfate, sodium carbonate, trisodium citrate, citric acid, neopentyl alcohol, PEG (polyethyleneglycol) 200, PEG 300, PEG 400, PEG 600, PEG 4000, PEG 550 monomethyl ether, PEG 1500 monomethyl ether, PEG 2000 monomethyl ether, PEG 5000 monomethyl ether, copolymers from ethylene oxide and propylene oxide (Pluronic F 108), D-sorbitol and sugar.

EXAMPLES 14 TO 18

The procedure described in Example 8 is repeated but using the formulations obtained according to each of Examples 9 to 13. Moreover, in addition to the storage test with the exclusion of air, a further storage test is conducted for 1 week at 25° C. in which the respective formulation is fully exposed to a moist laboratory atmosphere. The results obtained are set out in the following Table 3 (storage without air access) and Table 4 (storage with air access).

TABLE 3

| Whiteness/Colour | Example 14 | Example 15 | Example 16 | Example 17 | Example 18 |
|---|---|---|---|---|---|
| Filler | cyclodextrin | Zeolite I | Zeolite II | Bentonite | Urea/HCHO |
| Whiteness Colour | 134 white | 129 white | 132 white | 121 white | 136 white |

The results in Table 4 show that the good whiteness and colour properties of detergent compositions produced according to the present invention are retained even when the said detergent compositions are exposed to moist air for long periods.

TABLE 4

| Whiteness/Colour | Example 14 | Example 15 | Example 16 | Example 17 | Example 18 |
|---|---|---|---|---|---|
| Filler | cyclodextrin | Zeolite I | Zeolite II | Bentonite | Urea/HCHO |
| Whiteness Colour | 98 white | 95 white | 88 white | 72 white | 90 white |

EXAMPLES 19 TO 21

At 25° C., there are mixed 60 g of a yellow suspension of the compound of formula (1) containing 33% by weight of active substance and 67% by weight of water with 20 g of glycerine. The mixture is then stored at 60° C. for 24 hours. 20 g of a filler are then added and the mixture is again stored at 60° C. for 24 hours and thereafter at 25° C. for 24 hours.

The physical form and colour of the resulting product are then observed visually. The results obtained, using a variety of fillers, are set out in Table 5.

TABLE 5

| Filler/Aspect | Example 10 | Example 11 | Example 12 |
|---|---|---|---|
| Filler | Zeolite I | Zeolite II | Zeolite III |
| Product form | liquid | liquid | liquid |
| Colour | nearly white | nearly white | nearly white |

Zeolite I is $Na_{12}(AlO_2)_{12}(SiO_2)_{12}.27H_2O$; Zeolite II is $Na_{86}(AlO_2)_{86}(SiO_2)_{106}.264 H_2O$ and Zeolite III is $Na_2O.(Al_2O_3).(2-5)$ $SiO_2.(3,5-6)$ $H_2O$.

X-ray examination in each case confirmed the presence of the white crystal form shown in Table II.

EXAMPLE 22

At 25° C., there are mixed 100 g of a yellow suspension of the compound of formula (1) containing 30% by weight of active substance, 0.5% 1,2-propyleneglykol, 0.25% of an anionic polysaccharide and 69.25% by weight of water with 30 g of glycerine and stirred for 1 hour. The colour of the yellow suspension becomes lighter during mixing and the structure of the crystals changes from shapeless plates to rhombs.

X-ray examination confirmed the presence of the white crystal form shown in Table III.

TABLE I x-ray powder diffraction: 2θ values of modification N

| 2θ [°] | Intensity |
|---|---|
| 5.5° | very strong |
| 10.8° | medium |
| 13.9° | medium |
| 16.3° | weak |
| 18.0° | strong |
| 19.6° | medium |
| 20.4° | medium |
| 20.7° | weak |
| 21.5° | medium |
| 21.8° | very strong |
| 22.4° | medium |
| 23.0° | very weak |
| 23.6° | weak |
| 25.4° | medium |
| 26.2° | weak |
| 26.8° | very weak |
| 30.5° | weak |
| 33.9° | very weak |

TABLE II x-ray powder diffraction: 2θ values of modification O

| 2θ [°] | Intensity |
|---|---|
| 5.1° | very strong |
| 10.1° | medium |
| 13.8° | weak |
| 18.5° | weak |
| 19.5° | very weak |
| 20.2° | very strong |
| 23.4° | very weak |
| 23.7° | very weak |
| 24.1° | weak |
| 25.3° | very strong |
| 28.4° | weak |
| 30.4° | strong |
| 33.5° | very weak |
| 34.3° | very weak |

TABLE III x-ray powder diffraction: 2θ values of a binary mixture with modifications O and V

| 2θ [°] | Intensity |
|---|---|
| 5.1° | very strong |
| 9.5° | very weak |
| 9.9° | strong |
| 10.1° | medium |
| 11.5° | weak |
| 13.8° | very weak |
| 14.8° | weak |
| 15.9° | weak |
| 17.1° | very weak |
| 18.2° | weak |
| 18.5° | very weak |
| 19.8° | very strong |
| 20.2° | strong |
| 20.6° | weak |
| 24.7° | medium |
| 25.3° | strong |
| 25.4° | weak |
| 26.6° | very weak |
| 27.4° | very weak |
| 27.9° | very weak |
| 29.7° | medium |
| 30.4° | strong |

What is claimed is:

1. A formulation which comprises 30 to 60% by weight of a white crystal form of the compound having the formula (1)

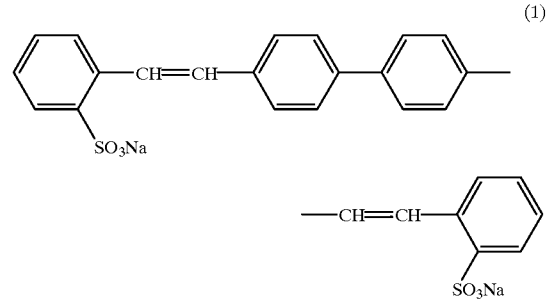

whose crystal form is characterized by an X-ray diffraction pattern which shows absorptions in the 2∅-area between 10 and 300 as follows:

1) 5.5° (very strong), 10.8° (medium), 13.9° (medium), 16.3° (weak), 18.0° (strong), 19.6° (medium), 20.4° (medium), 20.7° (weak), 21.5° (medium), 21.8° (very strong), 22.4° (medium), 23.0° (very weak), 23.6° (weak), 25.4° (medium), 26.2° (weak), 26.8° (very weak), 30.5° (weak), 33.9° (very weak), or 2) 5.1° (very strong), 10.1° (medium), 13.8° (weak), 18.5° (weak), 19.5° (very weak), 20.2° (very strong), 23.4° (very weak), 23.7° (very weak), 24.1° (weak), 25.3° (very strong), 28.4° (weak), 30.4° (strong), 33.5° (very weak), 34.3° (very weak), or 3) 5.1° (very strong), 9.5° (very weak), 9.9° (strong), 10.1° (medium), 11.5° (weak), 13.8° (very weak), 14.8° (weak), 15.9° (weak), 17.1° (very weak), 18.2° (weak), 18.5° (very weak), 19.8° (very strong), 20.2° (strong, 20.6° (weak), 24.7° (medium), 25.3° (strong), 25.4° (weak), 26.6° (very weak), 27.4° (very weak), 27.9° (very weak), 29.7° (medium), 30.4° (strong), and from 70 to 40% by weight of a polyhydroxy compound.

2. A formulation according to claim 1 which comprises from 40 to 60% by weight of the white crystal form of the compound having the formula (1), and from 60 to 40% by weight of a polyhydroxy compound.

3. A formulation according to claim 2 which comprises about 50% by weight of the white crystal form of the compound having the formula (1), and about 50% by weight of a polyhydroxy compound.

4. A formulation according to claim 1 in which polyhydroxy compound is a glycol or a triol.

5. A formulation according to claim 4 in which the glycol is ethylene glycol, diethylene glycol or propylene glycol.

6. A formulation according to claim 4 in which the triol is 1,2,6-hexanetriol, glycerine or an oligomer of glycerine.

7. A formulation according to claim 6 in which the oligomer of glycerine is a di-, tri- or polyglycerine.

8. A formulation according to claim 1 which also comprises an absorbent filler or carrier.

9. A liquid formulation according to claim 8 which contains from 5–40% by weight of the filler.

10. A solid formulation according to claim 8 which contains from 10–80% by weight of the filler.

11. A formulation according to claim 8 in which the absorbent filler or carrier is an inorganic salt, a further hydroxy group-containing compound or a solid carbohydrate.

12. A formulation according to claim 11 in which the absorbent filler or carrier sodium chloride, sodium sulfate, sodium carbonate or trisodium citrate.

13. A formulation according to claim 11 in which the further hydroxy group-containing compound is citric acid, neopentyl alcohol, PEG (polyethyleneglycol) 200, PEG 300, PEG 400, PEG 600, PEG 4000, PEG 550 monomethyl ether, PEG 1500 monomethyl ether, PEG 2000 monomethyl ether or PEG 5000 monomethyl ether.

14. A formulation according to claim 11 in which the solid carbohydrate is D-sorbitol or sugar.

15. A formulation according to claim 8 in which the absorbent filler or carrier is kaolin, a layer-lattice silicate, a Mg/Al silicate, montmorillonite, a zeolite, a highly dispersed silicic acid, cyclodextrin, a highly dispersed, solid, water-insoluble urea-formaldehyde resin comprising 1 mole of urea and 1.3 to 2 moles of formaldehyde, which is present in highly disperse form, having a mean particle diameter of 1 to 20 microns and having a specific BET surface of 5 to 100 m$^2$/g, an inorganic salt, a solid hydroxy group-containing compound or a solid carbohydrate.

16. A formulation according to claim 15 in which the Mg/Al silicate is bentonite.

17. A formulation according to claim 1 which also comprises one or more dispersants.

18. A formulation according to claim 17 in which the dispersant is anionic or non-ionic.

19. A formulation according to claim 18 in which the anionic dispersant is an alkylbenzenesulfonate, alkyl or alkenyl ether sulfonate salt, saturated or unsaturated fatty acid, alkyl or alkylene ether carboxylate salt, sulfonated fatty acid salt or ester, phosphate ester or sulfate ester.

20. A formulation according to claim 18 in which the nonionic dispersant is a polyoxyethylene alkyl or alkenyl ether, polyoxyethylene alkyl vinyl ether, polyoxypropylene alkyl or alkenyl ether, polyoxybutylene alkyl or alkenyl ether, higher fatty acid alkanolamide or alkylene oxide adduct or sucrose/fatty acid ester, fatty acid/glycol monoester or alkylamine oxide.

21. A formulation according to claim 20 in which the alkylene oxide adduct is a lower ethylene oxide adduct with a fatty alcohol.

22. A formulation according to claim 1 which also comprises an auxiliary selected from an anti-foam agent, an alkaline agent, a fabric softener, an anti-redeposition agent, an antioxidant, an auxiliary builder, a fragrance and an organic solvent.

23. A formulation according to claim 22 in which the auxiliary builder is polyacrylic acid and the organic solvent is a glycol.

24. A formulation according to claim 22 in which the organic solvent is ethylene glycol or a glycol-C$_1$–C$_4$alkyl ether or -ester.

25. A process for the production of a detergent composition comprising adding the formulation according to claim 1 to a dry detergent composition and then homogenising the mixture so obtained.

26. A process according to claim 25 in which the amount of the formulation added is from 0.01 to 10% by weight, based on the weight of the detergent composition.

27. A process for the production of a white crystal form of the compound having the formula:

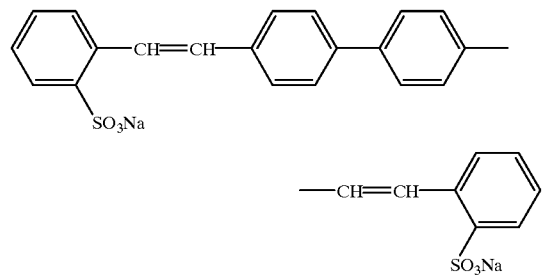

whose crystal form is characterized by an X-ray diffraction pattern which shows absorptions in the 2∅-area between 1° and 30° as follows:

1) 5.5° (very strong), 10.8° (medium), 13.9° (medium), 16.3° (weak), 18.0° (strong), 19.6° (medium), 20.4° (medium), 20.7° (weak), 21.5° (medium), 21.8° (very strong), 22.4° (medium), 23.0° (very weak), 23.6° (weak), 25.4° (medium), 26.2° (weak), 26.8° (very weak), 30.5° (weak), 33.9° (very weak), or 2) 5.1° (very strong), 10.1° (medium), 13.8° (weak), 18.5° (weak), 19.5° (very weak), 20.2° (very strong), 23.4° (very weak), 23.7° (very weak), 24.1° (weak), 25.3° (very strong), 28.4° (weak), 30.4° (strong), 33.5° (very weak), 34.3° (very weak), or 3) 5.1° (very strong), 9.5° (very weak), 9.9° (strong), 10.1° (medium), 11.5° (weak), 13.8° (very weak), 14.8° (weak), 15.9° (weak), 17.1° (very weak), 18.2° (weak), 18.5° (very weak), 19.8° (very strong), 20.2° (strong), 20.6° (weak), 24.7° (medium), 25.3° (strong), 25.4° (weak), 26.6° (very weak), 27.4° (very weak), 27.9° (very weak), 29.7° (medium), 30.4° (strong)

which process comprises contacting the compound having the formula (1) with ethanol or water, then adding a polyhydroxy compound in a weight ratio of 30 to 60% of the compound having the formula (1) to 70 to 40% of the polyhydroxy compound.

28. A process according to claim 27 in which the polyhydroxy compound is a glycol or a triol.

29. A process according to claim 28 in which the glycol is ethylene glycol, diethylene glycol or propylene glycol.

30. A process according to claim 28 in which the triol is 1,2,6-hexanetriol, glycerine or an oligomer of glycerine.

31. A process according to claim 30 in which the oligomer of glycerine is a di-, tri- or polyglycerine.

32. A process for the production of the formulation according to claim 27, further comprising mixing the white crystal form of the fluorescent whitening agent of formula (1) with glycerine, any absorbent filler, optional dispersant and optional auxiliaries, and then homogenising the mixture so obtained at room temperature or at elevated temperature.

33. A process according to claim 32 in which the homogenisation is conducted at 20–100° C.

34. A detergent composition comprising a white crystal form of the compound having the formula (1) produced by the process as defined in claim 27.

35. A white crystal form of the compound having the formula:

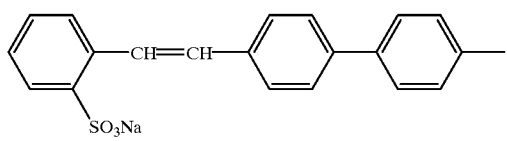

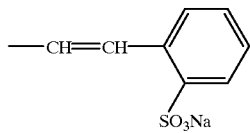

whose crystal form is characterized by an X-ray diffraction pattern which shows absorptions in the 2Ø-area between 1° and 30° as follows:

1) 5.5° (very strong), 10.8° (medium), 13.9° (medium), 16.3° (weak), 18.0° (strong), 19.6° (medium), 20.4° (medium), 20.7° (weak), 21.5° (medium), 21.8° (very strong), 22.4° (medium), 23.0° (very weak), 23.6° (weak), 25.4° (medium), 26.2° (weak), 26.8° (very weak), 30.5° (weak), 33.9° (very weak) or 2) 5.1° (very strong), 10.1° (medium), 13.8°(weak), 18.5° (weak), 19.5° (very weak), 20.2° (very strong), 23.4° (very weak), 23.7° (very weak), 24.1° (weak), 25.3° (very strong), 28.4° (weak), 30.4° (strong), 33.5° (very weak), 34.3° (very weak) or 3) 5.1° (very strong), 9.5° (very weak), 9.9° (strong), 10.1° (medium), 11.50° (weak), 13.8° (very weak), 14.8° (weak), 15.9° (weak), 17.1° (very weak), 18.2° (weak), 18.5° (very weak), 19.8°(very strong), 20.2° (strong), 20.6° (weak), 24.7 (medium), 25.3° (strong), 25.4° (weak), 26.6° (very weak), 27.4° (very weak), 27.9° (very weak), 29.7° (medium), 30.4° (strong).

* * * * *